(12) United States Patent
Lee et al.

(10) Patent No.: US 8,686,200 B2
(45) Date of Patent: Apr. 1, 2014

(54) PROCESS TO RECOVER ALCOHOL FROM AN ACIDIC RESIDUE STREAM

(75) Inventors: David Lee, Seabrook, TX (US); Fred Ronald Olsson, Corpus Christi, TX (US); Adam Orosco, Houston, TX (US); Nathan Powell, Waxahachie, TX (US); Manuel Salado, Seabrook, TX (US); Lincoln Sarager, Houston, TX (US); R. Jay Warner, Houston, TX (US); Trinity Horton, Houston, TX (US); Radmila Jevtic, Houston, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 344 days.

(21) Appl. No.: 13/094,588

(22) Filed: Apr. 26, 2011

(65) Prior Publication Data
US 2012/0277485 A1    Nov. 1, 2012

(51) Int. Cl.
C07C 27/04    (2006.01)
C07C 29/80    (2006.01)

(52) U.S. Cl.
USPC .......................................... 568/885; 568/913

(58) Field of Classification Search
USPC ....................................................... 568/885
See application file for complete search history.

(56) References Cited

U.S. PATENT DOCUMENTS

| | | |
|---|---|---|
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,769,329 A | 10/1973 | Knox et al. |
| 3,990,952 A | 11/1976 | Katzen et al. |
| 4,126,539 A | 11/1978 | Derr, Jr. et al. |
| 4,149,940 A | 4/1979 | Pinto |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulpranthipanja et al. |
| 4,352,940 A | 10/1982 | Adelman et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,443,639 A | 4/1984 | Pesa et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer et al. |
| 4,626,321 A | 12/1986 | Grethlein et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,842,693 A | 6/1989 | Wheldon |
| 4,886,905 A | 12/1989 | Larkins |
| 4,908,477 A | 3/1990 | Hartmann et al. |
| 4,961,826 A | 10/1990 | Grethlein et al. |
| 4,978,778 A | 12/1990 | Isshiki et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg et al. |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,198,592 A | 3/1993 | Van Beijnum et al. |
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,414,161 A | 5/1995 | Uhm et al. |
| 5,415,741 A | 5/1995 | Berg |
| 5,426,246 A | 6/1995 | Nagahara et al. |

(Continued)

FOREIGN PATENT DOCUMENTS

| | | |
|---|---|---|
| CN | 201768393 | 3/2011 |
| CN | 102228831 | 11/2011 |

(Continued)

OTHER PUBLICATIONS

International Search Report and Written Opinion mailed Jul. 6, 2012 in corresponding International Application No. PCT/US2011/059889.

(Continued)

*Primary Examiner* — Sikarl Witherspoon (57) ABSTRACT

Recovery of ethanol from a crude ethanol product obtained from the hydrogenation of acetic acid using a low energy process. The crude ethanol product is separated in a column to produce a distillate stream comprising ethyl acetate and a residue stream comprising ethanol, acetic acid, and water. The ethanol product is recovered from the residue stream.

29 Claims, 3 Drawing Sheets

(56) References Cited

U.S. PATENT DOCUMENTS

| | | |
|---|---|---|
| 5,437,770 A | 8/1995 | Berg |
| 5,445,716 A | 8/1995 | Berg |
| 5,449,440 A | 9/1995 | Rescalli et al. |
| 5,502,248 A | 3/1996 | Funk et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Grady et al. |
| 5,861,530 A | 1/1999 | Atkins et al. |
| 5,973,193 A | 10/1999 | Crane et al. |
| 5,993,610 A | 11/1999 | Berg |
| 6,040,474 A | 3/2000 | Jobson et al. |
| 6,093,845 A | 7/2000 | Van Acker et al. |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,375,807 B1 | 4/2002 | Nieuwoudt et al. |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,223,886 B2 | 5/2007 | Scates et al. |
| 7,226,886 B2 | 6/2007 | Jayaratne et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,732,173 B2 | 6/2010 | Mairal et al. |
| 7,744,727 B2 | 6/2010 | Blum et al. |
| 7,834,223 B2 | 11/2010 | Atkins |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 8,071,821 B2 | 12/2011 | Johnston et al. |
| 2003/0013908 A1 | 1/2003 | Horan et al. |
| 2003/0077771 A1 | 4/2003 | Verser et al. |
| 2005/0197506 A1 | 9/2005 | Scates et al. |
| 2006/0019360 A1 | 1/2006 | Verser et al. |
| 2006/0106246 A1 | 5/2006 | Warner et al. |
| 2006/0127999 A1 | 6/2006 | Verser et al. |
| 2007/0031954 A1 | 2/2007 | Mairal et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0221725 A1 | 9/2009 | Chorney et al. |
| 2009/0270651 A1 | 10/2009 | Zinobile et al. |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0137630 A1 | 6/2010 | Garton et al. |
| 2010/0197485 A1 | 8/2010 | Johnston et al. |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0190547 A1 | 8/2011 | Jevtic et al. |
| 2011/0190548 A1 | 8/2011 | Jevtic et al. |
| 2011/0275861 A1 | 11/2011 | Johnston et al. |
| 2011/0275862 A1 | 11/2011 | Johnston et al. |
| 2012/0010438 A1 | 1/2012 | Lee et al. |
| 2012/0010445 A1 | 1/2012 | Johnston et al. |

FOREIGN PATENT DOCUMENTS

| | | |
|---|---|---|
| CN | 102229520 | 11/2011 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0990638 | 4/2000 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| JP | 6-116182 | 4/1994 |
| JP | 2001-046874 | 2/2001 |
| WO | WO 83/03409 | 10/1983 |
| WO | WO 02/092541 | 11/2002 |
| WO | WO 2005/102513 | 11/2005 |
| WO | WO 2007/003897 | 1/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO 2009/105860 | 9/2009 |
| WO | WO 2010/014151 | 2/2010 |
| WO | WO 2010/055285 | 5/2010 |
| WO | WO 2011/053365 | 5/2011 |
| WO | WO 2011/097193 | 8/2011 |
| WO | WO 2011/097219 | 8/2011 |
| WO | WO 2011/097220 | 8/2011 |

(56) References Cited

FOREIGN PATENT DOCUMENTS

| WO | WO 2011/097227 A2 | 8/2011 |
|---|---|---|
| WO | WO 2011/140485 | 11/2011 |
| WO | WO 2012/006219 A2 | 1/2012 |
| WO | WO 2012/006228 | 1/2012 |
| WO | WO 2012/006499 | 1/2012 |

OTHER PUBLICATIONS

Hidetoshi Kita et al., "Synthesis of a zeolite NaA membrane for pervaporation of water/organic liquid mixtures", Journal of Materials Science Letters, 14 (1995) 206-208.

Marian Simo et al., "Adsorption/Desorption of Water and Ethanol on 3A Zeolite in Near-Adiabatic Fixed Bed", Ind. Eng. Chem. Res., 2009, 48, 9247-9260.

N. Calvar et al., "Esterification of acetic acid with ethanol: Reaction kinetics and operation in a packed bed reactive distillation column", Chemical Engineering and Processing, 46 (207) 1317-1323.

International Search Report and Written Opinion mailed Jun. 29, 2012 in corresponding International Application No. PCT/US2011/060014.

H. Constantin et al., "Influence of C-Sources on the Denitrification Rate of a High-Nitrate Concentrated Industrial Wastewater", Wat. Res. vol. 31, No. 3, 1997, pp. 583-589.

International Search Report and Written Opinion mailed Apr. 19, 2012 in corresponding International Application No. PCT/US2011/060019.

Y. Zhu et al., "Techno-economic Analysis for the Thermochemical Conversion of Lignocellulosic Biomass to Ethanol via Acetic Acid Synthesis", Apr. 1, 2009, pp. 1-71 (80 Pages).

International Search Report and Written Opinion mailed Jul. 30, 2012 in corresponding International Application No. PCT/US2012/035189.

International Search Report and Written Opinion mailed Aug. 2, 2012 in corresponding International Application No. PCT/US2012/035220.

International Search Report and Written Opinion mailed Aug. 6, 2012 in corresponding International Application No. PCT/US2012/035196.

Anonymous, "Studies in Extractive and Azeotropic Distillation Series: Study No. 4—Separation of Alcohols from the Acetate/Alcohol/Water Ternary by Extractive Distillation", May 9, 2008, pp. 1-9.

V. Ragaini et al., "Increasing the value of dilute acetic acid streams through esterification Part 1. Experimental analysis of the reaction zone", Applied Catalysis B: Environmental, vol. 64, 2006, pp. 66-71.

International Search Report and Written Opinion mailed Jul. 11, 2012 in corresponding International Application No. PCT/US2012/035203.

International Search Report and Written Opinion mailed Jul. 30, 2012 in corresponding International Application No. PCT/US2012/035273.

Tracy J. Benson et al., "Cellulose Based Adsorbent Materials for the Dehydration of Ethanol Using Thermal Swing Adsorption", Adsorption, vol. 11, 2005, pp. 697-701.

Yu Huang et al., "Low-Energy Distillation-Membrane Separation Process", Ind. Eng. Chem. Res., vol. 49, 2010, pp. 3760-3768.

Z. P. Xu et al., "Kinetics of Acetic Acid Esterification over Ion Exchange Catalysts", Canadian Journal of Chemical Engineering, vol. 74, Aug. 1, 1996, XP 009084826, pp. 493-500.

Kaj Jakobsson et al., "Modeling of a side reactor configuration combining reaction and distillation", Chemical Engineering Science, vol. 57, 2002, pp. 1521-1524.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

J. Jones, et al., Platinum Metals Review, vol. 44, No. 3, pp. 94-104 (Jul. 2000).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

Subramani et al., "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Witzeman and Agreda, "Safety and Performance Assessment of Ethanol/Diesel Blends (e-blend)" NREL/SR-540-34817, at p. 1-1, Sep. 2003.

International Search Report and Written Opinion for PCT/US2011/023276 mailed Sep. 2, 2011.

PROCESS TO RECOVER ALCOHOL FROM AN ACIDIC RESIDUE STREAM

FIELD OF THE INVENTION

The present invention relates generally to processes for producing alcohol and, in particular, to a process for recovering ethanol from an acidic residue stream.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acids, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition, when conversion is incomplete, acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol comprising hydrogenating acetic acid in a reactor in the presence of a catalyst to form a crude ethanol product, separating a portion of the crude ethanol product in a first distillation column to yield a first distillate comprising ethyl acetate and a first residue comprising ethanol, acetic acid and water, wherein a majority of the ethanol in the crude ethanol product that is fed to the column is removed in the first residue, and recovering ethanol from the first residue.

In a second embodiment, the present invention is directed to a process for producing ethanol comprising hydrogenating acetic acid in a reactor in the presence of a catalyst to form a crude ethanol product, separating a portion of the crude ethanol product in a first distillation column to yield a first residue comprising ethanol and a first distillate comprising ethanol and ethyl acetate, wherein the weight ratio of ethanol in the first residue to ethanol in the first distillate is at least 1:1, and recovering ethanol from the first residue.

In a third embodiment, the present invention is directed to a process for producing ethanol comprising providing a crude ethanol product comprising ethanol, ethyl acetate, water, and acetic acid, separating a portion of the crude ethanol product in a first distillation column to yield a first distillate comprising ethyl acetate and a first residue comprising ethanol, acetic acid and water, wherein a majority of the ethanol in the crude ethanol product that is fed to the column is removed in the first residue, and recovering ethanol from the first residue.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Introduction

The present invention relates to processes for recovering ethanol produced by hydrogenating acetic acid in the presence of a catalyst. The hydrogenation reaction produces a crude ethanol product that comprises ethanol, water, ethyl acetate, acetic acid, and other impurities. The processes of the present invention involve separating the crude ethanol product in a first column into a residue stream comprising ethanol, water, and acetic acid and a distillate stream comprising ethyl acetate. Subsequently, the ethanol is removed from the residue stream to yield an ethanol product. Advantageously, this separation approach results in reducing energy requirements to recover ethanol from the crude ethanol product.

In recovering ethanol, the processes of the present invention use one or more distillation columns. In preferred embodiments, the residue stream comprises a substantial portion of the ethanol, water, and the acetic acid from the crude ethanol product. The residue stream, for example, may comprise at least 50% of the ethanol from the crude ethanol product, and more preferably at least 70%. In terms of ranges, the residue stream may comprise from 50% to 97.5% of the ethanol from the crude ethanol product, and more preferably from 70% to 97.5%. The amount of ethanol from the crude ethanol recovered in the residue may be greater than 97.5%, e.g. up to 99.9%, when the ethyl acetate concentration in the crude ethanol product is less than 2 wt. %. In some embodiments, depending on the ethyl acetate concentration, taking too much ethanol in the residue may cause undesirable leakage of ethyl acetate in the residue. It is preferred that ethyl acetate is not withdrawn in the residue and may be present in very low amounts, e.g., less than 100 wppm or less than 50 wppm.

In preferred embodiments, the residue stream comprises a substantial portion of the water and the acetic acid from the crude ethanol product. The residue stream may comprise at least 80% of the water from the crude ethanol product, and more preferably at least 90%. In terms of ranges, the residue stream preferably comprises from 80% to 99.4% of the water from the crude ethanol product, and more preferably from 90% to 99.4%. The residue stream may comprise at least 85% of the acetic acid from the crude ethanol product, e.g., at least 90% and more preferably about 100%. In terms of ranges, the residue stream preferably comprises from 85% to 100% of the acetic acid from the crude ethanol product, and more preferably from 90% to 100%. In one embodiment, substantially all of the acetic acid is recovered in the residue stream.

The residue stream comprising ethanol, water, and acetic acid may be further separated to recover ethanol. In one preferred embodiment, the water and acetic acid may be removed as another residue stream in a separate distillation column.

In an exemplary embodiment, the energy requirements by the initial column in the process according to the present invention may be less than 5.5 MMBtu per ton of refined ethanol, e.g., less than 4.5 MMBtu per ton of refined ethanol or less than 3.5 MMBtu per ton of refined ethanol.

The distillate from the initial column comprises light organics, such as ethyl acetate and acetaldehyde. Removing these components from the crude ethanol product in the initial column provides an efficient means for removing light organics. In addition, the light organics are not carried over with the ethanol when multiple columns are used, thus reducing the formation of byproducts from the light organics. In one embodiment, the light organics are returned to the reactor, where the acetaldehyde and the ethyl acetate are converted to additional ethanol. In some embodiments, the light organics may be separated so that one stream comprising primarily acetaldehyde or ethyl acetate is returned to the reactor. In another embodiment, the light organics may be purged from the system.

Hydrogenation of Acetic Acid

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from other available carbon source. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also US Publ. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by converting carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain N or Pro. The Saint-Gobain N or Pro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Ethanol Recovery

Exemplary ethanol recovery systems in accordance with embodiments of the present invention are shown in FIGS. 1, 2, 3, and 4. Each hydrogenation system 100 provides a suitable hydrogenation reactor and a process for separating ethanol from the crude reaction mixture according to an embodiment of the invention. System 100 comprises reaction zone 101 and separation zone 102. Reaction zone 101 comprises reactor 103, hydrogen feed line 104 and acetic acid feed line 105. Separation zone 102 comprises a separator 106 and one or more distillation columns.

Hydrogen and acetic acid are fed to a vaporizer 109 via lines 104 and 105, respectively, to create a vapor feed stream in line 110 that is directed to reactor 103. In one embodiment, lines 104 and 105 may be combined and jointly fed to the vaporizer 109. The temperature of the vapor feed stream in line 110 is preferably from 100° C. to 350° C., e.g., from 120° C. to 310° C. or from 150° C. to 300° C. Any feed that is not vaporized is removed from vaporizer 109, and may be recycled or discarded. In addition, although line 110 is shown as being directed to the top of reactor 103, line 110 may be directed to the side, upper portion, or bottom of reactor 103. Further modifications and additional components to reaction zone 101 and separation zone 102 are described below.

Reactor 103 contains the catalyst that is used in the hydrogenation of the carboxylic acid, preferably acetic acid. In one embodiment, one or more guard beds (not shown) may be used upstream of the reactor, optionally upstream of vaporizer 109, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 103 via line 111.

The crude ethanol product stream may be condensed and fed to a separator 106, which, in turn, forms a vapor stream 112 and a liquid stream 113. In some embodiments, separator 106 may comprise a flasher or a knockout pot. The separator 106 may operate at a temperature of from 20° C. to 250° C., e.g., from 30° C. to 225° C. or from 60° C. to 200° C. The pressure of separator 106 may be from 50 kPa to 2000 kPa, e.g., from 75 kPa to 1500 kPa or from 100 kPa to 1000 kPa. Optionally, the crude ethanol product in line 111 may pass through one or more membranes to separate hydrogen and/or other non-condensable gases.

The vapor stream 112 exiting separator 106 may comprise hydrogen and hydrocarbons, and may be purged and/or returned to reaction zone 101. As shown, vapor stream 112 is combined with the hydrogen feed 104 and co-fed to vaporizer 109. In some embodiments, the returned vapor stream 112 may be compressed before being combined with hydrogen feed 104.

The liquid stream 113 from separator 106 is withdrawn and directed as a feed composition to the side of first distillation column 107, also referred to as an "light ends column" In one embodiment, the contents of liquid stream 113 are substantially similar to the crude ethanol product obtained from the reactor, except that the composition has been depleted of hydrogen, carbon dioxide, methane or ethane, which have been removed by separator 106. Accordingly, liquid stream 113 may also be referred to as a crude ethanol product. Exemplary components of liquid stream 113 are provided in Table 2. It should be understood that liquid stream 113 may contain other components, not listed in Table 2.

TABLE 2

COLUMN FEED COMPOSITION
(Liquid Stream 113)

|  | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 45 | 5 to 30 | 10 to 30 |
| Ethyl Acetate | <35 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, liquid stream 113 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol product in line 111 or in liquid stream 113 may be further fed to an esterification reactor, hydrogenolysis reactor, or combination thereof. An esterification reactor may be used to consume acetic acid present in the crude ethanol product to further reduce the amount of acetic acid to be removed. Hydrogenolysis may be used to convert ethyl acetate in the crude ethanol product to ethanol.

Figure 1:
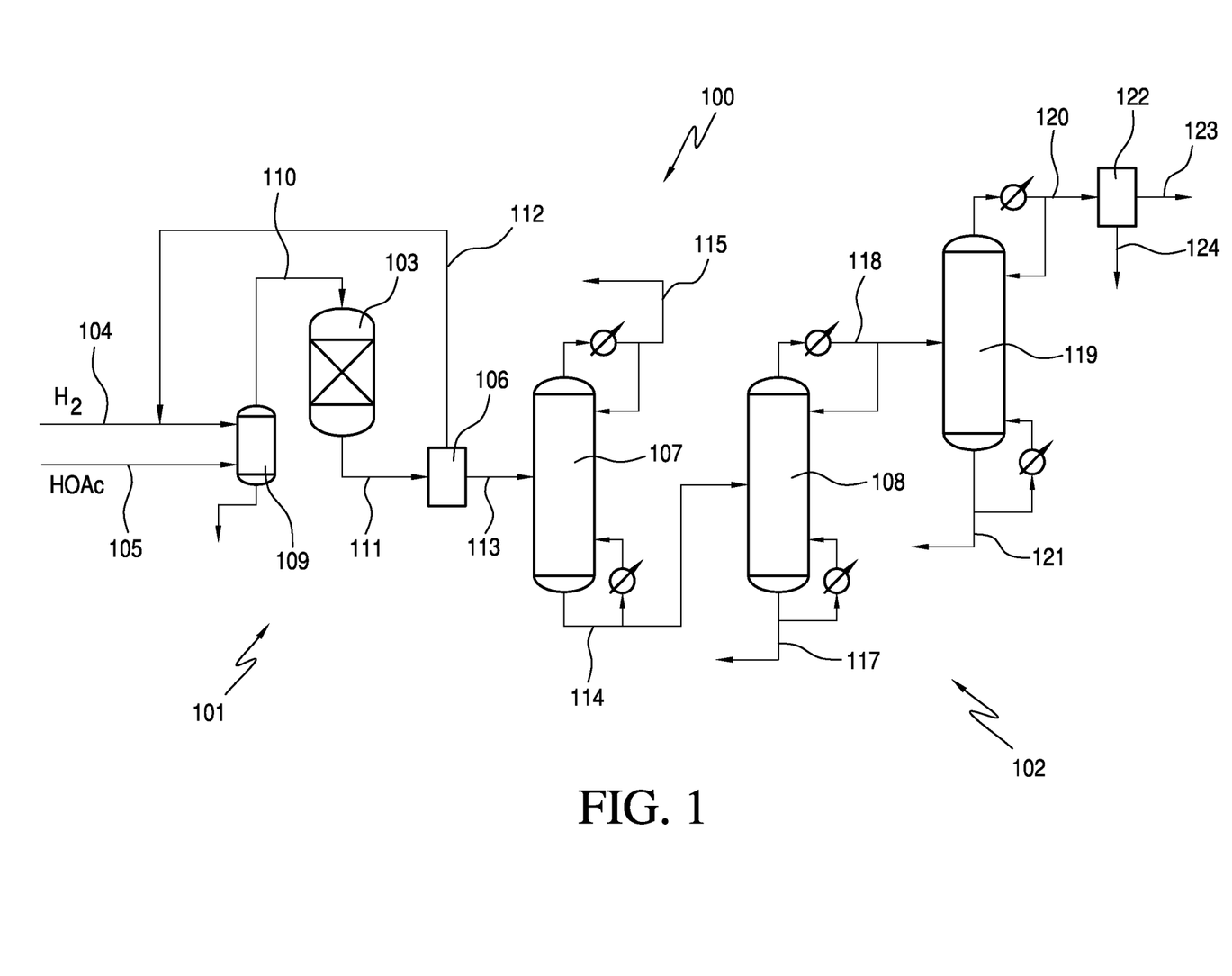
FIG. 1 is a schematic diagram of an ethanol production system with multiple distillation columns to recover ethanol including an acid separation column in accordance with one embodiment of the present invention.

In the embodiment shown in FIG. 1, liquid stream 113 is introduced in the upper part of first column 107, e.g., upper half or upper third. In one embodiment, no entrainers are added to first column 107. In first column 107, a weight majority of the ethanol, water, acetic acid, and other heavy components, if present, are removed from liquid stream 113 and are withdrawn, preferably continuously, as residue in line 114. First column 107 also forms an overhead distillate, which is withdrawn in line 115, and which may be condensed and refluxed, for example, at a ratio of from 30:1 to 1:30, e.g., from 10:1 to 1:10 or from 1:5 to 5:1. The overhead distillate in stream 115 preferably comprises a weight majority of the ethyl acetate from liquid stream 113.

When column 107 is operated under about 170 kPa, the temperature of the residue exiting in line 116 preferably is from 70° C. to 155° C., e.g., from 90° C. to 130° C. or from 100° C. to 110° C. The base of column 107 may be maintained at a relatively low temperature by withdrawing a residue stream comprising ethanol, water, and acetic acid, thereby providing an energy efficiency advantage. The temperature of the distillate exiting in line 115 from column 107 preferably at 170 kPa is from 75° C. to 100° C., e.g., from 75° C. to 83° C. or from 81° C. to 84° C. In some embodiments, the pressure of first column 107 may range from 0.1 kPa to 510 kPa, e.g., from 1 kPa to 475 kPa or from 1 kPa to 375 kPa. Exemplary components of the distillate and residue compositions for first column 107 are provided in Table 3 below. It should also be understood that the distillate and residue may also contain other components, not listed in Table 3. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN

|  | Conc. (wt. %) | Conc. (wt. %) | Conc. (wt. %) |
|---|---|---|---|
| Distillate |  |  |  |
| Ethyl Acetate | 10 to 85 | 15 to 80 | 20 to 75 |
| Acetaldehyde | 0.1 to 70 | 0.2 to 65 | 0.5 to 65 |
| Acetal | <0.1 | <0.1 | <0.05 |
| Acetone | <0.05 | 0.001 to 0.03 | 0.01 to 0.025 |
| Ethanol | 3 to 55 | 4 to 50 | 5 to 45 |
| Water | 0.1 to 20 | 1 to 15 | 2 to 10 |
| Acetic Acid | <2 | <0.1 | <0.05 |
| Residue |  |  |  |
| Acetic Acid | 0.01 to 35 | 0.1 to 30 | 0.2 to 25 |
| Water | 25 to 70 | 30 to 65 | 35 to 60 |
| Ethanol | 10 to 75 | 15 to 70 | 20 to 65 |

In an embodiment of the present invention, column 107 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 114 to water in the distillate in line 115 may be greater than 1:1, e.g., greater than 2:1. The weight ratio of ethanol in the residue to ethanol in the distillate may be greater than 1:1, e.g., greater than 2:1

The amount of acetic acid in the first residue may vary depending primarily on the conversion in reactor 103. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

In some embodiments, the separation in first column 107 may be conducted without the addition of an azeotrope or extractive agent.

The distillate preferably is substantially free of acetic acid, e.g., comprising less than 1000 ppm, less than 500 ppm or less than 100 ppm acetic acid. The distillate may be purged from the system or recycled in whole or part to reactor 103. In some embodiments, the distillate may be further separated, e.g., in a distillation column (not shown), into an acetaldehyde stream and an ethyl acetate stream Either of these streams may be returned to the reactor 103 or separated from system 100 as a separate product.

Some species, such as acetals, may decompose in first column 107 such that very low amounts, or even no detectable amounts, of acetals remain in the distillate or residue.

In addition, an equilibrium reaction between acetic acid/ethanol and ethyl acetate may occur in the crude ethanol product after it exits reactor 103. Depending on the concentration of acetic acid in the crude ethanol product, this equilibrium may be driven toward formation of ethyl acetate. This reaction may be regulated through the residence time and/or temperature of the crude ethanol product.

The columns shown in FIGS. 1-4 may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

Figure 2:
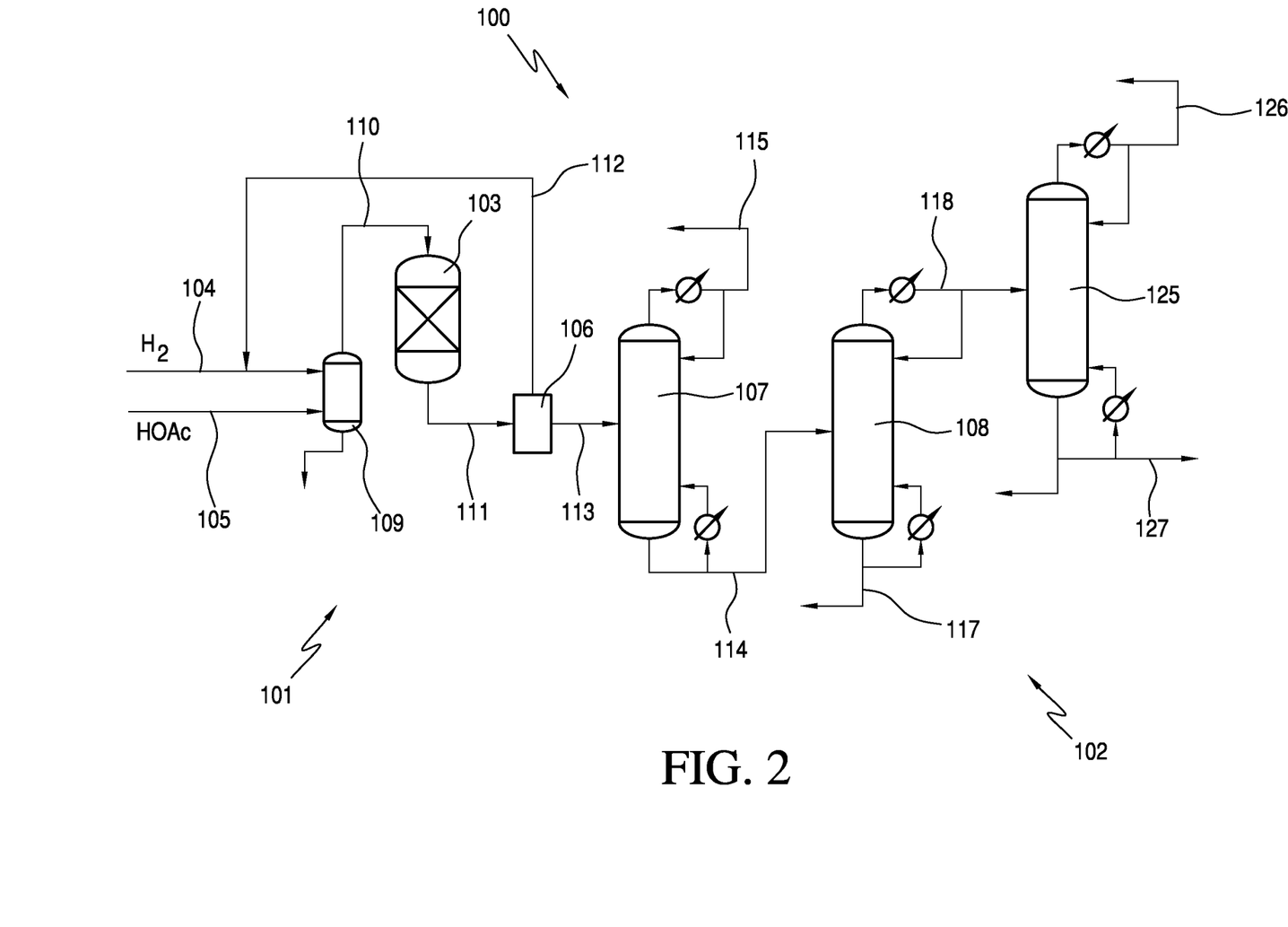
FIG. 2 is a schematic diagram of an ethanol production system with multiple distillation columns to recover ethanol including a secondary light ends column in accordance with one embodiment of the present invention.
Figure 3:
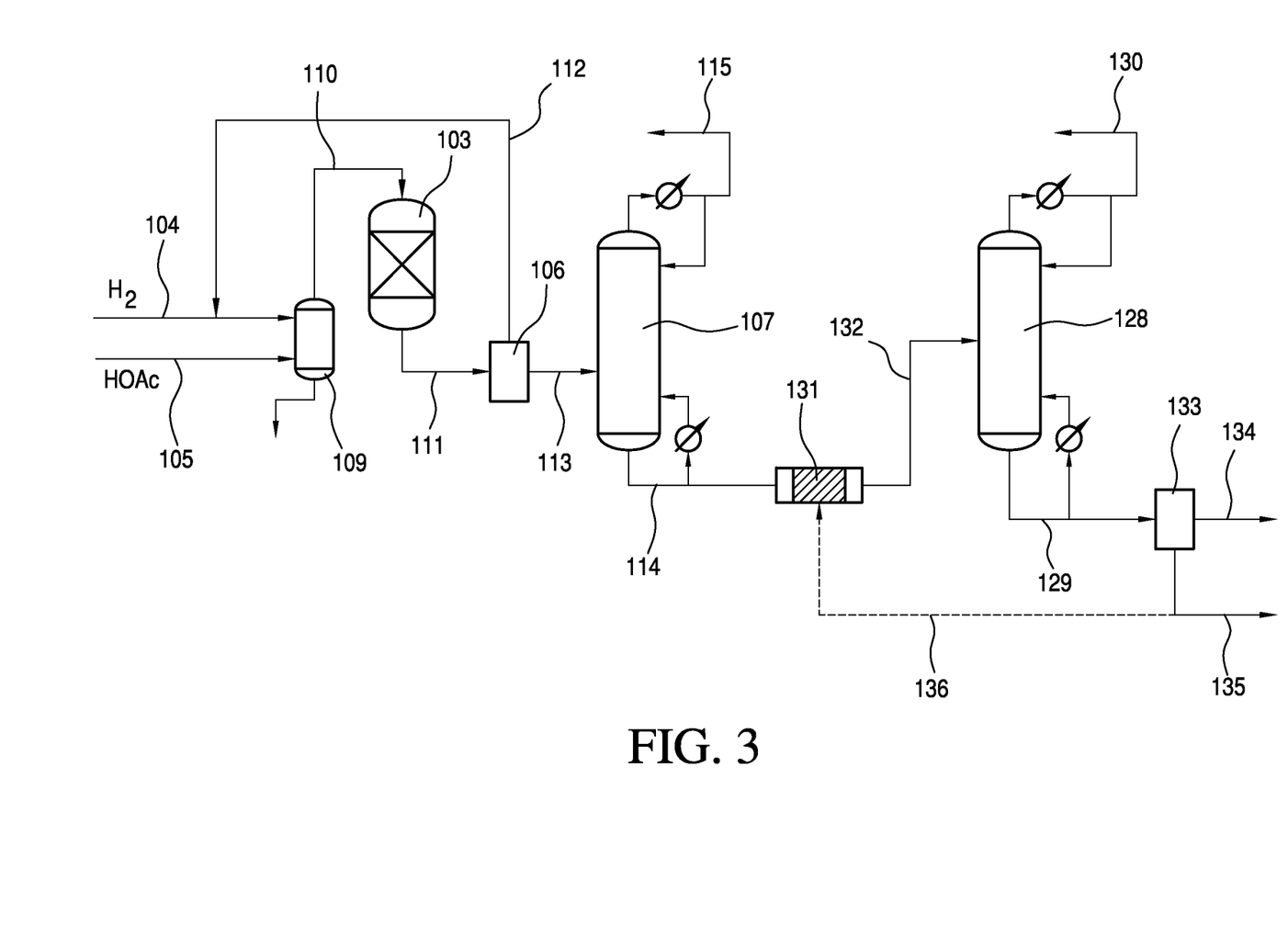
FIG. 3 is a schematic diagram of an ethanol production system with an esterification reactor in accordance with one embodiment of the present invention.

To recover ethanol, the residue in line 114 may be further separated depending on the concentration of acetic acid and/or ethyl acetate. In most embodiments of the present invention, residue in line 114 is further separated in a second column 108. In FIGS. 1 and 2, the second column is referred to as an "acid separation column," because the second residue 117 comprises acetic acid and water. An acid separation column may be used when the acetic acid concentration in the first residue is greater than 1 wt. %, e.g., greater than 5 wt. %. In FIG. 3, the second column is referred to as an "light ends column," because the second residue comprises ethanol. A light ends column may be used when the ethyl acetate concentration from the first residue is greater than 5 wt. %. ethyl acetate may form in first residue as a result of the equilibrium reaction with acetic acid and ethanol, or may be formed using an esterification reactor as shown in FIG. 3, or formed using an reactive distillation column.

In FIGS. 1 and 2, the first residue in line 114 is introduced to second column 108, e.g., acid separation column, preferably in the top part of column 108, e.g., top half or top third. Second column 108 yields a second residue in line 117 comprising acetic acid and water, and a second distillate in line 118 comprising ethanol. Second column 108 may be a tray column or packed column. In one embodiment, second column 108 is a tray column having from 5 to 150 trays, e.g., from 15 to 50 trays or from 20 to 45 trays. Although the temperature and pressure of second column 108 may vary, when at atmospheric pressure the temperature of the second residue exiting in line 117 from second column 108 preferably is from 95° C. to 130° C., e.g., from 100° C. to 125° C. or from 110° C. to 120° C. The temperature of the second distillate exiting in line 118 from second column 108 preferably is from 60° C. to 105° C., e.g., from 75° C. to 100° C. or from 80° C. to 100° C. The pressure of second column 108 may range from 0.1 kPa to 510 kPa, e.g., from 1 kPa to 475 kPa or from 1 kPa to 375 kPa. Exemplary components for the distillate and residue compositions for second column 108 are provided in Table 4 below. It should be understood that the distillate and residue may also contain other components, not listed in Table 4.

TABLE 4

| ACID SEPARATION COLUMN 108 | | | |
|---|---|---|---|
| | Conc. (wt. %) | Conc. (wt. %) | Conc. (wt. %) |
| Second Distillate | | | |
| Ethanol | 70 to 99.9 | 75 to 98 | 80 to 95 |
| Ethyl Acetate | <10 | 0.001 to 5 | 0.01 to 3 |
| Acetaldehyde | <5 | 0.001 to 1 | 0.005 to 0.5 |
| Water | 0.1 to 30 | 1 to 25 | 5 to 20 |

TABLE 4-continued

ACID SEPARATION COLUMN 108

|  | Conc. (wt. %) | Conc. (wt. %) | Conc. (wt. %) |
|---|---|---|---|
| Second Residue |  |  |  |
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.001 to 5 | <2 |

The weight ratio of ethanol in the second distillate in line 118 to ethanol in the second residue in line 117 preferably is at least 35:1. In one embodiment, the weight ratio of water in the second residue 117 to water in the second distillate 118 is greater than 2:1, e.g., greater than 4:1 or greater than 6:1. In addition, the weight ratio of acetic acid in the second residue 117 to acetic acid in the second distillate 118 preferably is greater than 10:1, e.g., greater than 15:1 or greater than 20:1. Preferably, the second distillate in line 118 is substantially free of acetic acid and may only contain, if any, trace amounts of acetic acid. A reduced concentration of acetic acid in line 118 advantageously provides an ethanol product that also has no amount or a trace amount of acetic acid. Preferably, the second distillate in line 118 contains substantially no ethyl acetate.

The remaining water from the second distillate in line 118 may be removed in further embodiments of the present invention. Depending on the water concentration, the ethanol product may be derived from the second distillate in line 118. Some applications, such as industrial ethanol applications, may tolerate water in the ethanol product, while other applications, such as fuel applications, may require an anhydrous ethanol. The amount of water in the distillate of line 118 may be closer to the azeotropic amount of water, e.g., at least 4 wt. %, preferably less than 20 wt. %, e.g., less than 12 wt. % or less than 7.5 wt. %. Water may be removed from the second distillate in line 118 using several different separation techniques. Particularly preferred techniques include the use of distillation column, membranes, adsorption units and combinations thereof.

As shown, the second distillate in line 118 is fed to a third column 119, e.g., ethanol product column, for separating the distillate into a third distillate (ethanol distillate) in line 120 and a third residue (water residue) in line 121. Second distillate in line 118 may be introduced into the lower part of column 119, e.g., lower half or lower third. Third distillate 120 of third column 119 preferably is refluxed, for example, at a reflux ratio of from 1:10 to 10:1, e.g., from 1:3 to 3:1 or from 1:2 to 2:1. Third residue in line 121 preferably is removed from the system. Third column 119 is preferably a tray column as described above and preferably operates at atmospheric pressure. The temperature of the third distillate exiting from third column 119 preferably is from 60° C. to 110° C., e.g., from 70° C. to 100° C. or from 75° C. to 95° C. The temperature of the third residue exiting from third column 119 preferably is from 70° C. to 115° C., e.g., from 80° C. to 110° C. or from 85° C. to 105° C., when the column is operated at atmospheric pressure.

In one embodiment, the third distillate in line 120 may comprise from 75 to 96 wt. % ethanol and less than 12 wt. % water. The organics from the second distillate in line 118, if any, generally carry over and concentrate in the third distillate (line 120). Water residue in line 121 may be purged from the system 100 as necessary. Depending on the desired ethanol application and on the concentration of organics in the third distillate, the resulting third distillate in line 120 may be withdrawn from the system as the finished ethanol product. For some ethanol applications, it may be desirable to remove residual water from the third distillate in line 120. Residual water removal may be accomplished, for example, using one or more adsorption units, membranes, molecular sieves, extractive distillation units, or a combination thereof. Suitable adsorption units include pressure swing adsorption systems and thermal swing adsorption units.

As shown in FIG. 1, an adsorption unit 122 may be provided to remove a water in water stream 123 from the third distillate in line 120 thus producing an anhydrous ethanol stream 124 comprising 97 wt. % or more ethanol, e.g., at least 98 wt. % ethanol or at least 99.5 wt. % ethanol. The adsorption unit 122 may employ a suitable adsorption agent such as a zeolite. In one preferred embodiment adsorption unit 122 is a pressure swing adsorption (PSA) unit that is operated at a temperature from 30° C. to 160° C., e.g., from 80° C. to 140° C., and a pressure of from 0.01 kPa to 550 kPa, e.g., from 1 to 150 kPa. The PSA unit may comprise two to five beds. Adsorption unit 122 may remove at least 95% of the water from the third distillate in line 120, and more preferably from 95% to 99.9% of the water from the third distillate in line 120. Water stream 123 may be combined with any other water stream from system 100 and preferably is removed from the system. The water stream may also comprise ethanol, in which case it may be desirable to feed all or a portion of the water stream back to column 119 or other separation device for further ethanol recovery.

In one aspect, not shown, one or more adsorption units, membranes, molecular sieves, extractive distillation columns, or a combination thereof may replace ethanol product column 119. In this aspect, for example, the second distillate in line 118 may be fed directly to adsorption unit 122. Column 119 may be replaced by one or more of these other separation units, for example, when the second distillate in line 118 contains less than about 7 wt. % water, e.g., less than 5 wt. % water.

Depending on the amount of water and acetic acid contained in the second residue of second column 108, line 117 may be treated in one or more of the following processes. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from first residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent or to hydrolyze an ester-containing stream in a hydrolysis unit.

In other embodiments, for example where second residue in line 117 comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent)

may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue in line 113 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the second residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

In some embodiments, where the second distillate comprises some ethyl acetate, primarily due to the equilibrium reaction with acetic acid, a further distillation column may be used to separate ethyl acetate and ethanol as shown in FIG. 2. FIG. 2, shows a third column 125, referred to as a secondary light ends column, for removing ethyl acetate from the second distillate in line 118 into a third distillate in line 126. The third distillate may be purged from system or recycled in whole or part to reactor 103, along with first distillate in line 115. The third residue in line 127 from third column 125 may comprise ethanol and optionally water. The third residue may be further processed to recover ethanol with a desired amount of water, for example, using the ethanol product column as described above in FIG. 1. An ethanol product column, adsorption unit, membrane or combination thereof, may be used to further remove water from third residue in line 127 as necessary.

In FIG. 3, separation zone 102 further comprises a second column 128 referred to as an "light ends column" In some embodiments, first residue in line 114 may comprise lower amounts of acetic acid, due to higher conversions in reactor 103. As discussed above, an esterification reaction may occur that consumes the acetic acid in the first residue which results in increased ethyl acetate concentrations. Although ethyl acetate may not be withdrawn in the first residue from first column 107, the feed to second column 128 may contain ethyl acetate. In addition, because of the lower acetic acid concentration it may not be necessary to remove the acetic acid using a separate distillation column.

Although a non-catalyzed esterification may produce some ethyl acetate, it may be more preferred to react the acetic acid in the first residue in line 114 in an esterification reactor 131 before being fed to second column 128, as shown in FIG. 3. Optionally, second column 128 may be a reactive distillation column, which may replace the esterification reactor.

The esterification reaction may be conducted in the liquid or vapor phase at a reaction temperature that ranges from 10° C. to 150° C., e.g., from 20° C. to 100° C., or from 30° C. to 80° C. The pressure in the esterification may vary and generally ranges from 10 kPa to 2000 kPa, e.g., from 50 kPa to 1000 kPa, or from 100 kPa to 500 kPa.

Acid-catalyzed esterification catalysts may be used with some embodiments of the present invention. The catalyst should be thermally stable at reaction temperatures. Suitable catalysts may be solid acid catalysts comprising an ion exchange resin, zeolites, Lewis acid, metal oxides, inorganic salts and hydrates thereof, and heteropoly acid and salts thereof. Silica gel, aluminum oxide, and aluminum phosphate are also suitable catalysts. Acid catalysts include, but are not limited to, sulfuric acid, and tosic acid. In addition, Lewis acids may also be used as esterification catalysts, such as scandium(III) or lanthanide(III) triflates, hafnium(IV) or zirconium(IV) salts, and diarylammonium arenesulfonates. The catalyst may also include sulfonated (sulphonic acid) ion-exchange resins (e.g., gel-type and macroporous sulfonated styrene-divinyl benzene IERs), sulfonated polysiloxane resins, sulfonated perfluorinated (e.g., sulfonated poly-perfluoroethylene), or sulfonated zirconia.

In esterification reactor 131, acetic acid preferably reacts with ethanol to form ethyl acetate, thus yielding an ester enriched stream 132. Ester enriched stream 132 comprises more ethyl acetate than first residue in line 114, e.g., at least 5 wt. % more ethyl acetate, at least 15 wt. % more ethyl acetate, or at least 30 wt. % more ethyl acetate. In addition, ester enriched stream 132 preferably comprises less acetic acid than first residue in line 114. In one embodiment, ester enriched stream 132 may comprise less than 10 wt. % acetic acid, e.g., less than 5 wt. % or less than 1 wt. %. In terms of ranges, ester enriched stream 132 may comprise from 0.01 to 10 wt. % acetic acid, e.g., from 0.05 to 5 wt. %, or from 0.05 to 1 wt. %.

In FIG. 3, ester enriched stream 132 is introduced to light ends column 128. Second column 128 yields a second residue in line 129 comprising ethanol and water, and a second distillate in line 130 comprising ethyl acetate. Second residue in 129 may be further separated in one or more adsorption units 133 or membranes, to produce a water stream 134 and an ethanol product stream 135. Optionally, a portion of ethanol product in line 136, which preferably comprises less than 50% of ethanol product stream 135, may be fed to esterification reactor 131. When a reactive distillation column is used, the portion of ethanol in line 136 may be fed to the reactive distillation column.

The ethanol product produced by the process of the present invention may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 5.

TABLE 5

| FINISHED ETHANOL COMPOSITIONS | | | |
|---|---|---|---|
| Component | Conc. (wt. %) | Conc. (wt. %) | Conc. (wt. %) |
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 7, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entireties of which is incorporated herein by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, an example is provided below. It should be understood that this example is for illustrative purposes only and is not to be construed as limiting the invention in any manner.

EXAMPLE

The following examples were prepared with ASPEN Plus 7.1 simulation software to test various feed composition and separation systems.

A crude ethanol product comprising 56 wt. % ethanol, 38 wt. % water, 2% acetaldehyde, 2% ethyl acetate, 1 wt. % acetic acid, and 1 wt. % other organics is fed into a first column. This first column contains 75 trays with feed located at the 8th tray from the top. The reflux rate is 30 times the distillate rate. The distillate and residue compositions are shown in Table 6.

TABLE 6

| Component (wt. %) | Distillate | Residue |
|---|---|---|
| Ethanol | 17.3 | 58 |
| Water | 6.2 | 39.7 |
| Ethyl Acetate | 39.9 | 0.01 |
| Acetic Acid | <0.01 | 1.1 |
| Acetaldehyde | 30 | <0.01 |
| Other organics | 6.6 | 1.2 |

The residue stream is further processed by a second distillation column. It contains 75 trays with the feed location mid-way between the top and the bottom. The distillate and residue compositions are shown in Table 7.

TABLE 7

| Component (wt. %) | Distillate | Residue |
|---|---|---|
| Ethanol | 91.8 | <0.01 |
| Water | 6.2 | 98.9 |
| Ethyl Acetate | 0.01 | <0.01 |
| Acetic Acid | <0.01 | 1.1 |
| Acetaldehyde | <0.01 | <0.01 |
| Other organics | 2 | <0.01 |

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, comprising:
hydrogenating acetic acid in a reactor in the presence of a catalyst to form a crude ethanol product;
separating a portion of the crude ethanol product in a first distillation column to yield a first distillate comprising ethyl acetate and a first residue comprising ethanol, acetic acid and water, wherein a weight majority of the ethanol, acetic acid, and water in the crude ethanol product that is fed to the column is removed in the first residue; and
recovering ethanol from the first residue.

2. The process of claim 1, wherein at least 70% of the ethanol in the crude ethanol product is removed in the first residue stream.

3. The process of claim 1, wherein the first residue exits the first distillation column at a temperature from 70 to 155° C.

4. The process of claim 1, wherein the first residue comprises 10 to 75 wt. % ethanol, 0.01 to 35 wt. % acetic acid, and 25 to 70 wt. % water.

5. The process of claim 1, wherein the first distillate comprises 10 to 85 wt. % ethyl acetate, 0.1 to 70 wt. % acetaldehyde, less than 55 wt. % ethanol, and less than 20 wt. % water.

6. The process of claim 1, further comprising returning at least a portion of the first distillate to the reactor.

7. The process of claim 1, wherein the weight ratio of ethanol in the first residue to ethanol in the first distillate is greater than 1:1.

8. The process of claim 1, further comprising separating a portion of the first residue in a second distillation column to yield a second residue comprising acetic acid and water and a second distillate comprising ethanol.

9. The process of claim 8, further comprising recovering acetic acid from the second residue and returning at least a portion of the recovered acetic acid to the reactor.

10. The process of claim 8, wherein the second residue comprises 0.1 to 10 wt. % acetic acid, the process further comprising the step of neutralizing or reacting the acetic acid from the second residue.

11. The process of claim 8, further comprising separating at least a portion of the second distillate in a third distillation column into a third distillate comprising ethanol and a third residue comprising water.

12. The process of claim 11, wherein the third distillate comprises 75 to 96 wt. % ethanol, less than 12 wt. % water, less than 1 wt. % acetic acid, and less than 5 wt. % ethyl acetate.

13. The process of claim 8, further comprising reducing the water content of the second distillate to yield an ethanol product stream with reduced water content.

14. The process of claim 13, wherein the ethanol product stream comprises less than 3 wt. % water.

15. The process of claim 8, further comprising the steps of:
separating at least a portion of the second distillate in a third distillation column into a third distillate comprising ethanol and a third residue comprising water; and
removing residual water from the third distillate using an adsorption unit to form the ethanol product stream.

16. The process of claim 8, further comprising removing water from at least a portion of the second distillate in an adsorption unit to yield an ethanol product stream having a lower water content than the at least a portion of the second distillate.

17. The process of claim 8, further comprising the steps of:
separating at least a portion of the second distillate in a third distillation column into a third distillate comprising ethanol and a third residue comprising water; and
separating the third distillate with a membrane into a permeate stream comprising water and a retentate stream comprising ethanol and less water than the third distillate.

18. The process of claim 8, further comprising separating at least a portion of the second distillate with a membrane into a permeate stream comprising water and a retentate stream comprising ethanol and less water than the at least a portion of the second distillate.

19. The process of claim 8, further comprising extracting at least a portion of the second distillate with one or more extractive agents to yield an ethanol product stream with a reduced water content.

20. The process of claim 1, wherein at least some of the acetic acid in the first residue is reacted with ethanol to form an ester enriched stream.

21. The process of claim 20, wherein the first residue is fed to an esterification reactor comprising an acidic catalyst.

22. The process of claim 20, further comprising separating a portion of the ester enriched stream in a second distillation column to yield a second residue comprising ethanol and water and a second distillate comprising ethyl acetate.

23. The process of claim 1, further comprising feeding at least a portion of the first residue to a reactive distillation column to produce a distillate comprising ethyl acetate and a residue comprising ethanol and water.

24. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

25. A process for producing ethanol comprising:
hydrogenating acetic acid in a reactor in the presence of a catalyst to form a crude ethanol product;
flashing the crude ethanol product to yield a vapor stream comprising hydrogen, and a liquid stream comprising ethanol, ethyl acetate, water, and acetic acid;
separating the liquid stream in a first distillation column to yield a first residue comprising ethanol and acetic acid, and a first distillate comprising ethanol and ethyl acetate, wherein the weight ratio of ethanol in the first residue to ethanol in the first distillate is greater than 1:1; and
recovering ethanol from the first residue.

26. The process of claim 25, wherein the first residue comprises 10 to 75 wt. % ethanol, 0.01 to 35 wt. % acetic acid, and 25 to 70 wt. % water.

27. The process of claim 25, wherein the first distillate comprises 10 to 85 wt. % ethyl acetate, 0.1 to 70 wt. % acetaldehyde, less than 55 wt. % ethanol, and less than 20 wt. % water.

28. The process of claim 25, further comprising returning at least a portion of the first distillate to the reactor.

29. A process for producing ethanol, comprising:
providing a crude ethanol product comprising hydrogen, ethanol, ethyl acetate, water, and acetic acid;
flashing the crude ethanol product to yield a vapor stream comprising hydrogen, and a liquid stream comprising ethanol, ethyl acetate, water, and acetic acid;
separating the liquid stream in a first distillation column to yield a first distillate comprising ethyl acetate and a first residue comprising ethanol, acetic acid and water, wherein a majority of the ethanol and acetic acid in the crude ethanol product that is fed to the column is removed in the first residue; and
recovering ethanol from the first residue.

* * * * *